United States Patent [19]
Korhonen et al.

[11] Patent Number: 5,541,342
[45] Date of Patent: Jul. 30, 1996

[54] SEPARATION OF AMINO ACIDS, AMINO-ACID-BASED MONOMER, AND PROCESS FOR THE PREPARATION THEREOF, AS WELL AS POLYMER MATERIAL AND PROCESS FOR THE PREPARATION THEREOF

[75] Inventors: Pirjo Korhonen, Kantvik, Finland; Björn Ekberg, Lund, Sweden; Lauri Hietaniemi, Siuntio, Finland

[73] Assignees: Bio-Swede AB, Lund, Sweden; Cultor Oy, Kantvik, Finland

[21] Appl. No.: 244,726

[22] PCT Filed: Dec. 18, 1992

[86] PCT No.: PCT/SE92/00878
§ 371 Date: Sep. 12, 1994
§ 102(e) Date: Sep. 12, 1994

[87] PCT Pub. No.: WO93/13034
PCT Pub. Date: Jul. 8, 1993

[30] Foreign Application Priority Data

Dec. 20, 1991 [SE] Sweden .................................. 9103785

[51] Int. Cl.$^6$ ..................... C07D 207/00; C07D 209/00
[52] U.S. Cl. ............................................ 548/532; 548/402
[58] Field of Search .................................... 548/532, 402

[56] References Cited

PUBLICATIONS

Angew., Chem Suppl. (1982), pp. 425–433; Weinstein.
Anderson et al., J. Chromatoqr, (1990) 513; Abstract Only Considered.
O'Shannessy et al., J. Chromatoqr., (1989) 470(2), Abstract Only Considered.
O'Shannessy et al. Anal. Biochem., (1989) 177(i), Abstract Only Considered.
Davankov, V. A., Chemical Abstracts, vol. 98 (1983) 108037e 98:108037e.
O'Shannessy et al., Anal. Biochem., vol. 177, pp. 144–149 (1989).
Wulff, American Chemical Society, vol. 308, pp. 186–230 (1986).
Fischer et al., J. Am. Chem. Soc., vol. 113, pp. 9358–9360 (1991).
Shea et al., J. Am. Chem. Soc., vol. 108, pp. 1091–1093 (1986).
Danvankov, Pure & Appl. Chem., vol. 54, No. 11, pp. 2159–2168 (1982).
Liardon et al., J. Agric. Food Chem., vol. 35, pp. 661–667 (1987).
Julian et al., J. Am. Chem. Soc., vol. 70, pp. 180–183 (1948).
Hein et al., J. Am. Chem. Soc., vol. 84, pp. 4487–4494 (1962).
Davankov, et al., Chirality, vol. 2, pp. 208–210 (1990).
Lefebvre et al., J. of Liq. Chrom., vol. 1, pp. 766–774 (1978).
Einarsson et al., Anal. Chem., vol. 59, pp. 1191–1195 (1987).

*Primary Examiner*—Johann Richter
*Attorney, Agent, or Firm*—Birch, Stewart, Kolasch & Birch, LLP

[57] ABSTRACT

A process for separating a selected amino acid (enantiomer) from a mixture of different compounds including other amino acids is disclosed, in which process the mixture is contacted with a polymer material which is composed of cross-linked, amino-acid-based monomer units, said polymer material containing a molecular print of the selected amino acid. In the molecular print there is also bound a diastereomeric complex between the selected amino acid (enantiomer), a divalent metallic ion and the amino-acid-based monomer unit. Also the amino-acid-based monomer unit and a process for preparation thereof, as well as a polymer material composed of the amino-acid-based monomer unit and a process for the preparation thereof are disclosed.

19 Claims, 2 Drawing Sheets

SEPARATION OF AMINO ACIDS, AMINO-ACID-BASED MONOMER, AND PROCESS FOR THE PREPARATION THEREOF, AS WELL AS POLYMER MATERIAL AND PROCESS FOR THE PREPARATION THEREOF

This is a 371 of PCT SE92/00878, filed Dec. 18, 1992.

BACKGROUND OF THE INVENTION

1. Field of the Invention

The present invention relates to a process for separating amino acids, an amino-acid-based monomer, and a process for the preparation thereof, as well as a polymer material, and a process for the preparation thereof.

2. Description of the Related Art

Amino acids are structural elements of one of the most important types of molecules in nature, viz. proteins. It is most essential that amino acids of high purity are available, inter alia, as the starting material in different syntheses and as components in infusions.

Moreover, most amino acids are chiral, and with few exceptions only one enantiomer is of interest. The access to efficient purification methods for amino acids is essential in order to prepare such compounds of high, especially optical, purity.

Today a number of fundamentally different processes are available for purifying amino acids with regard to both the type of amino acid and the enantiomeric form. These processes may be divided into three main types: chemical, chromatographic and enzymatic. However, only a few of them are suitable for nonderivatized amino acids which are mainly of interest in industrial applications, since derivatization of such relatively inexpensive fine chemicals is unrealistic from the economic point of view.

The present invention relates to a new, preferably chromatographic, process of purifying nonderivatized amino acids.

The molecular imprinting technique implies preparing a synthetic polymer of desired affinity for a certain molecule (the so-called print molecule) (See B. Ekberg and K. Mosbach, Trends in Biotechnology, Vol. 7, 92–96, 1989; G. Wulff, American Chemical Society Symp. Ser., Vol. 308, 186–230, 1986). The polymer is composed of monomer units and intermediate cross-linking agents. The network contains a print of the print molecule. The preparation can be divided into three main steps, as shown in FIG. 1. First, there are formed chemical interactions between the monomers (of the same or different chemical structures) and the print molecule in a selected solvent. These interactions may be both noncovalent and covalent. After adding cross-linking agents and an initiator, there is formed in the second step a polymer round the complex of monomer and print molecule. This results in a "mould" round the print molecule. The last step comprises extraction for removing the print molecule from the polymer, whereby an affinity seat remains in the polymer. This affinity seat is a molecular print of the print molecule in the polymer.

The molecular print means that a form of adsorbtive "memory" for the print molecule has been formed in the polymer. This implies that the print molecule will be better adsorbed to the polymer than a molecule which is structurally related to the print molecule (see FIG. 2). Depending on the type of print molecule, a substrate- or enantio-selective polymer is obtained. This can then be used for specific separation of the print molecule in a subsequent separation process, e.g. liquid chromatography. In the extraction step, the print molecule can be recovered.

Fundamentally, the functional monomer and also the cross-linking agent are selected according to the interactions that are desired between this and the print molecule. The interactions can be either noncovalent or (reversibly) covalent. The covalent bonding is not as general as the noncovalent. Furthermore, more drastic chemical conditions must be applied to remove the print molecule during the extraction step. When noncovalent bondings exist, significantly milder extraction conditions can be applied. The noncovalent bonding is the most general type of bonding, since there are more interactions between the print molecule and monomers at the same time as a mixture of different monomers can be used. (See L. I. Andersson, "Molecular recognition in synthetic polymers; A study of the preparation and use of molecularly imprinted polymers, thesis, Applied Biochemistry, University of Lund, 1990).

The molecular imprinting technique has been applied to prepare polymers having the above described selectively adsorptive properties for amino acid derivatives (but not nonderivatised amino acids which are the subject matter of this invention) and smaller peptides (See B. Ekberg and K. Mosbach; G. Wulff; L. I. Andersson; D. O'Shannessy, B. Ekberg and K. Mosbach, J. of Anal. Biochem., Vol. 470, 391–399, 1989; L. I. Andersson and K. Mosbach, J. of Chrom., Vol. 516, 313–322, 1990), β-blockers (See L. Fischer, R. Müller, B. Ekberg and K. Mosbach, J. Am. Chem. Soc., Vol. 113, 9358–9360, 1991), carbohydrate derivatives and carbohydrates (See G. Wulff), ketones (See K. J. Shea and T. K. Dougherty, J. Am. Chem., Soc., Vol. 108, 1091–1093, 1986), etc.

SUMMARY OF THE INVENTION

Purification of nonderivatised amino acids by means of polymers prepared according to the molecular imprinting technique has not been reported so far, inter alia owing to solubility problems in organic solvents. The present invention makes it possible to purify nonderivatised amino acids by means of polymers prepared according to a method in which the molecular imprinting technique is partly utilised.

A process for separating a large number of different amino acids, both from each other and resolution of the respective racemate, has been developed by V. A. Davankov et al. (See V. A. Davankov, Pure & Appl. Chem., Vol. 54, No. 11, 2159–2168, 1982; V. A. Davankov, J. D. Navratil and H. F. Walton, "Ligand Exchange Chromatography," CRC Press Inc., Boca Raton, Fla., 1988). The process is based on the forming of a diastereomeric complex between an optically active solid phase (e.g. containing an amino acid derivative) and an amino acid enantiomer in the presence of a metallic ion (e.g. copper (II)), see FIG. 3. These diastereomeric complexes vary in stability. This difference can be used to separate amino acids (enantiomers) in a liquid chromatography process in which the amino acid (enantiomer) forming the weakest diastereomeric complex is eluted first. Davankov et al have proved that by this method, a number of amino acids (enantiomers) can be separated.

The present invention relates to a new technique of separating amino acids and their enantiomers by means of a polymer prepared according to a new method which is a combination of the fundamentally completely different molecular imprinting technique and the so-called Davankov-method. In this manner, the two separating properties, the molecular print of the nonderivatised amino acid enantiomer and the stability of the diastereomeric complex, are combined in one and the same polymer, which results in increased separation power in the new polymer (see FIG. 4).

The present invention thus relates to a process for separating a selected amino acid (enantiomer) from a mixture of different components including other amino acids. In this process, the mixture of amino acid is contacted with a polymer material which is composed of cross-linked, amino-acid-based monomer units, said polymer material containing a molecular print of the selected amino acid (enantiomer), in which molecular print a diastereomeric complex may be formed between the amino acid, a divalent metallic ion and the amino-acid-based monomer unit.

The invention also relates to an amino-acid-based monomer which consists of N-methacrylamidomethyl-L-proline or N-methacrylamidomethyl-D-proline.

The invention also relates to a process for preparing N-methacrylamidomethyl-L-proline or N-methacrylamidomethyl-D-proline, in which L-proline or D-proline, formalin and methacrylamide are condensed under alkaline conditions.

Moreover, the invention relates to a polymer material for use in separating a selected amino acid (enantiomer) from a mixture. This polymer material is composed of a cross-linked, amino-acid-based monomer unit and contains a molecular print of the selected amino acid, said molecular print further containing a diastereomeric complex between the amino acid, a divalent metallic ion and the amino-acid-based monomer unit.

Finally, the invention also relates to a process for preparing a polymer material, said process comprising a) preparation of a diastereomeric metallic ion complex between an amino-acid-based monomer unit and the selected amino acid (enantiomer), b) polymerization of the diastereomeric complex in the presence of a cross-linking agent, and c) removal of the selected amino acid from the polymerized diastereomeric complex for forming a molecular print of the selected amino acid in the polymer material.

BRIEF DESCRIPTION OF THE DRAWINGS

The invention is described by means of, inter alia, the accompanying figures and the examples below.

DETAILED DESCRIPTION OF THE INVENTION

Figure 1:
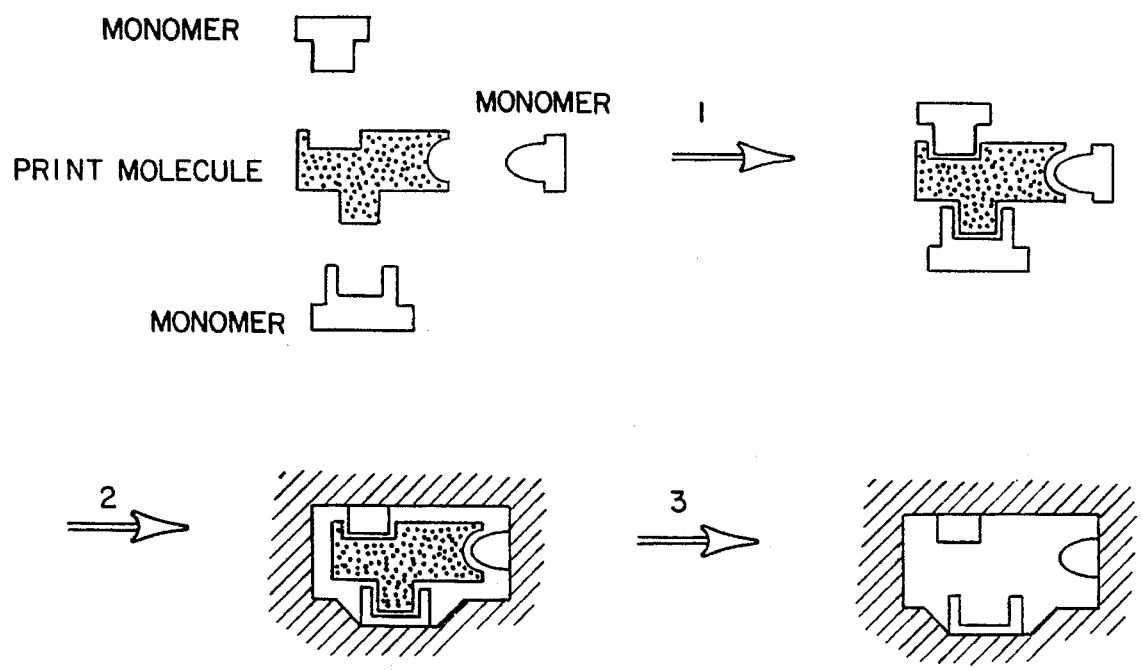
FIG. 1 illustrates the principle of preparing a molecular print in a polymer.
Figure 2:
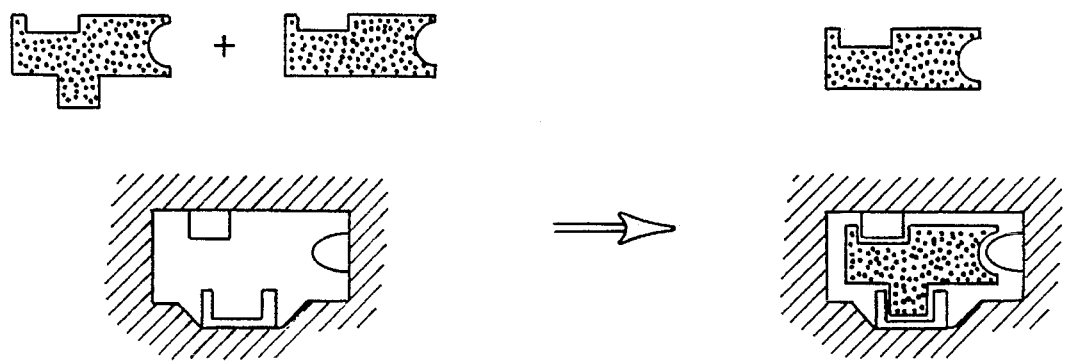
FIG. 2 illustrates the use of the polymer for separating two different compounds.
Figure 3:
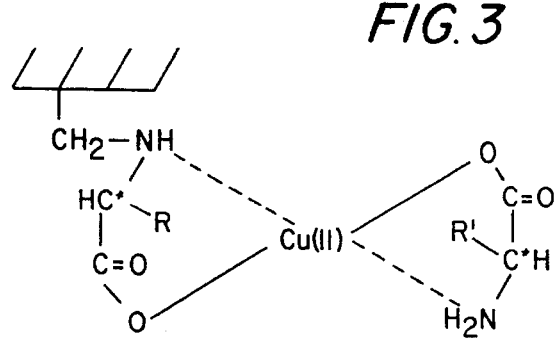
FIG. 3 illustrates a diastereomeric complex between an optically active solid phase and an amino acid enantiomer in the presence of a copper (II) ion (according to V. A. Davankov; V. A. Davankov, J. D. Navratil and H. F. Walton).
Figure 4:
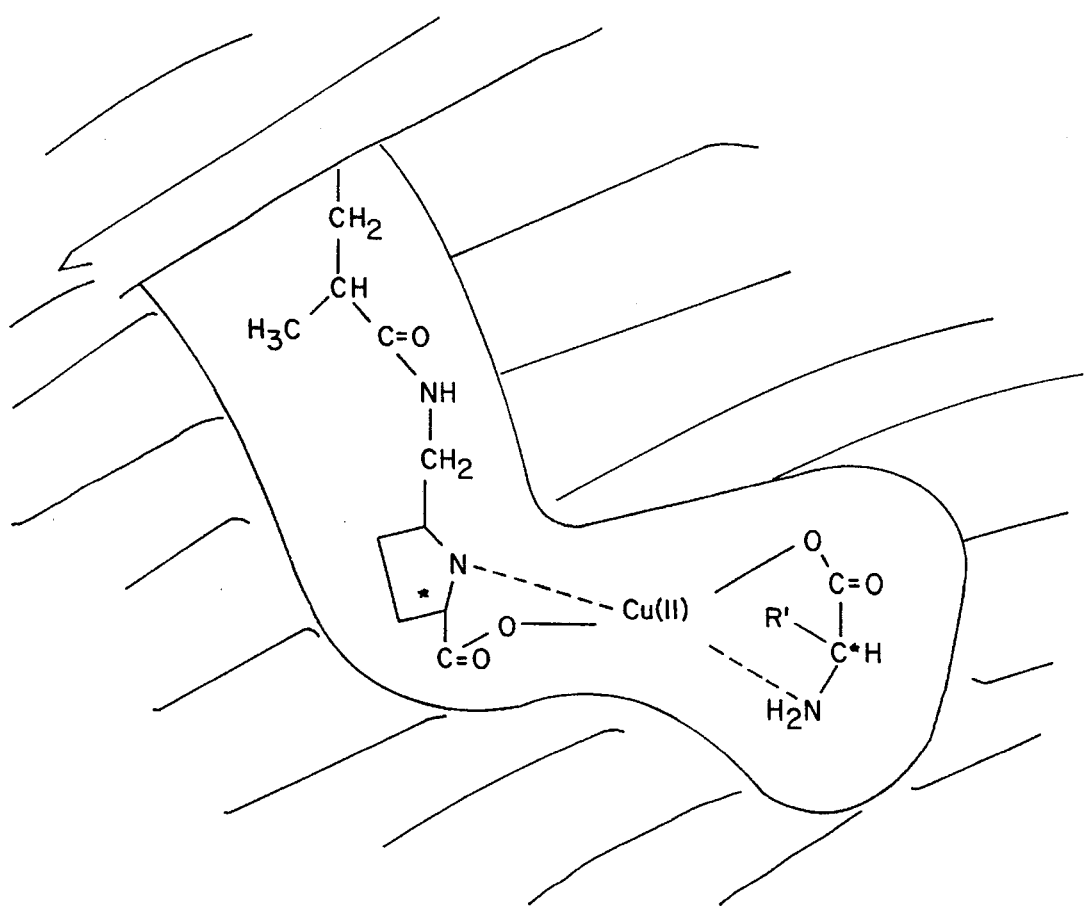
FIG. 4 shows a polymer material according to the invention before removal of the amino acid enantiomer used as a print molecule (to the right in the figure).
Figure 5:
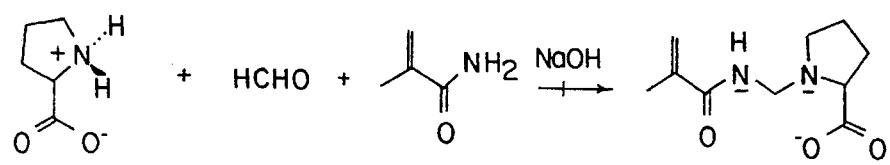
FIG. 5 shows the reaction formula for preparing N-methacrylamidomethyl-L-proline.

According to the reaction in FIG. 5, a polymerizable (unsaturated) derivative of L-proline is prepared, N-methacrylamidomethyl-L-proline. The method is distinguished by the reactants being simple and readily available substances (proline, methacrylic acid amide and formaldehyde), and by the reaction occurring under alkaline conditions. Similarly, the corresponding D-enantiomer can be prepared.

When carrying out this reaction, it is important that the pH value is adapted so as to be higher than the $pK_{a2}$ value of proline. Secondary amino acids, e.g. proline, and similar substances (pipecolic acid, hydroxy proline, allohydroxy proline, azetidine carboxylic acid and porretine) are stable with respect to racemisation under basic conditions (See R. Liardon and M. Friedman, J. Agric. Food Chem., Vol. 35, 661–667, 1987), which means that the optical configuration of the amine can be maintained during the reaction. The racemisation will, however, be significant if primary amines are used instead.

The complex between the polymerizable derivative of L-proline, a divalent metallic ion and a selected amino acid (enantiomer) is prepared by intermixing the components at a controlled pH value. If the L-enantiomer of the proline derivative is used in combination with D-proline, the resulting metallic ion complex will be more stable than if the L-enantiomer of the proline derivative is used in combination with L-proline (See V. A. Davankov, V. R. Meyer and Maya Rais, Chirality, Vol. 2, 208–210, 1990). This combination of enantiomers in the complex introduces a selectivity for D-proline in the resulting polymer. To attain a selectivity for L-proline, the complex between the D-proline derivative, a divalent metallic ion and L-proline can be prepared in a similar manner. The proline derivative can also be used for the preparation of polymers with selectivity for an amino acid enantiomer other than proline. This can be carried out by preparing the complex between the proline derivative and an enantiomer of an amino acid other than proline.

The selected amino acid (enantiomer) can be any naturally occurring or synthetic amino acid.

A number of different metallic ions can serve as the coordinating centre in the diastereomeric complex. As mentioned above, Cu(II) is the most frequently described, but corresponding complexes with Mn(II), Fe(II), Co(II), Zn(II), Cd(II) and Ni(II) have also been described (see V. A. Davankov, J. D. Navratil and H. F. Walton). In view of the industrial applicability of the present invention, the purification of amino acids carried out with smaller toxic metallic ions other than Cu(II) is of great interest.

The polymer can be prepared by polymerizing the selected diastereomeric complex in an organic solvent in the presence of a cross-linking agent, e.g. ethylene glycol dimethacrylate, while using an initiator, e.g. azoisobutyronitrile. The selection of the initiator allows both thermal and photolytic (366 nm) initiation (see D. O'Shannessy, B. Ekberg and K. Mosbach). The complex may also be polymerized in water in the presence of water-soluble cross-linking agents, e.g. N,N'-methylenebisacrylamide, while using an initiator system based on ammonium peroxodisulphate.

Chromatographic separation of amino acids (enantiomers) on the prepared polymers can be carried out while using distilled water, water-based solutions and organic solvents as mobile phases.

EXAMPLE 1

Preparation of N-methacrylaminomethyl-L-proline

At room temperature, 3.00 g (0.026 mole) L-proline (Sigma), 1.04 g (0.026 mole) NaOH, and 2.21 g (0.026 mole) methacrylic acid amide (Merck) are dissolved in 50 ml of water in a 100 ml round-bottomed flask fitted with a tight plastic cork and a magnetic stirrer. 2.0 ml (0.026 mole) formaldehyde (Merck) is added during cooling with ice/water bath (about +4° C.). The reaction solution is stirred for 4 h and is then allowed to take room temperature. The reaction process can be followed by means of thin-layer chromatography on DC-Alufolien, Kieselgel 60 $F_{254}$ (Merck) with methanol p.a. as the eluant. Detection is carried out by colouring with iodine. L-proline: $R_F$ 0.35, methacrylic acid amide: $R_F$ 0.83, N-methacrylamidomethyl-L-proline: $R_F$ 0.56, formaldehyde is not coloured with iodine.

The pH of the reaction mixture is adjusted to 8.5 with 2M sulphuric acid, and subsequently the reaction solution is evaporated at reduced pressure. The remaining oil is dried in a desiccator under vacuum above NaOH and is then dissolved in 40 ml methanol (Merck, max. 0.01% $H_2O$). $Na_2SO_4$ is precipitated. Before this salt is filtered off, 10 g molecular sieve (Merck, 3 Å) is added. The remaining solution is evaporated at reduced pressure to a volume of about 30 ml. This reaction solution is purified in a chromatographic process on a silica gel column (Kieselgel 60, Merck, 4×60 cm) with methanol as the eluant. After combining suitable fractions and evaporating at reduced pressure, 3.00 g (corresponding to a yield of 60% of the theoretical maximum) uncoloured substance is obtained. $R_F$ 0.56 (methanol). Melting point: 90°–92° C. $[\alpha]_D^{22}$ –71.2° (c=0.773 in methanol/distilled water, 3/1).

$^1$H-NMR ($CF_3COOD$): 1 H, 5.1 ppm, s; 1 H, 4.8 ppm, s; 1 H, 4.1 ppm, d, $^2J$=12.45 Hz, AB-spin system; 1 H, 4.02 ppm, d, 2J=12.16 Hz, AB-spin system, 1 H, 3.73 ppm, m; 1 H, 3.1 ppm, m; 1 H, 4 H, 1.5 ppm, m; 3 H, 1.1 ppm, s.

$^{13}C$-NMR: R—COO$^-$, 175.9 ppm; RHN—CO—R, 174.4 ppm; $(R_2)(R_1)C=CH_2$, 138.3 ppm; $(R_2)(R_1)C=CH_2$, 128.1 ppm; $NCH(CH_2)COO^-$), 67.6 ppm; N—$CH_2$—N, 62.2 ppm; $NCH_2CH_2$, 56.2 ppm; $CHCH_2CH_2$, 30.6 ppm; $CH_2CH_2\ CH_2$, 24.8 ppm.

Preparation of N-methacrylamidomethyl-L-proline - Cu(II) - D-proline Complex 1.71 g (7.3 mmole) N-methacrylamidomethyl-L-proline, 1.165 g (7.3 mole) $CuSO_4$ and 0.84 g (7.3 mole) D-proline are dissolved in 20 ml of distilled water. The pH is adjusted by means of 1M NaOH to 6.85. The solution is evaporated at reduced pressure and is dried overnight in a desiccator. Then the dry residue is dissolved in 30 ml methanol, and after filtering off inorganic salts, the methanol solution is evaporated at reduced pressure. 2.95 g (corresponding to a yield of 98% of the theoretical maximum) blue-coloured substance is obtained. $R_F$ 0.51 (methanol). Melting point: 206°–208° C. IR (cm$^{-1}$): 3500–3200, 2960–2850; 1680–1640 (strong); 1610–1550 (strong); 1550–1520; 1470–1430; 1420–1300.

Preparation of Polymer 2.95 g (7.2 mmol) N-methacrylamidomethyl-L-proline - Cu(II) - D-proline complex is dissolved together with 7.77 g (39.2 mmole) ethylene glycol dimethacrylate (Merck) in 13 ml methanol in a test tube. The solution is passed by nitrogen gas and before the test tube is provided with a tight-fitting cork, 95 mg (0.58 mmole) azoisobutyronitrile (Merck) is added. The polymerization is then allowed to proceed at 65° C. overnight.

The formed polymer is crushed by hand in a mortar and is then ground in a mechanical mortar device (Retsch, Haan, Germany) for 5 min. The material is sieved through a 25 µm sieve. Subsequently the material is allowed to sediment in two turns in 95% ethanol, while removing the supernatant. The sediment is carefully washed with 1/1 95% ethanol/distilled water and 1M $NH_3$ in order to remove D-proline and is then dried in a desiccator overnight. Amino acid analysis after hydrolysis (6M HCl, 24 h, 110° C.) of a sample of the polymer proved that the polymer contains 52% of the theoretical amount of the proline derivative.

Chromotographic Evaluation

The obtained polymer material is packed in an HPLC steel column (100×4.6 mm) in distilled water at a pressure of 200 bar. The column is placed in an HPLC device (Kontron, Switzerland) and equilibrated in 1M $NH_3$ at a flow rate of 0.25 ml/min, and detection is carried out by measuring the absorbency at 260 nm. 400 µg D,L-proline is injected in 20 µl distilled water. $k'_L$=0.40, $k'_D$=1.37. Separation factor: 3.4. Moreover, the same amount of the following racemates is injected; D,L-threonine, D,L-phenylalanine, D,L-serine and D,L-valine. These racemates were not resolved. The separation factor for the corresponding resolution of D,L-proline with a polymer prepared according to the Davankov method was 1.54 (See B. Lefebvre, R. Audebert and C. Quivoron, J. of Liq. Chrom., 1, 761–774, 1978).

EXAMPLE 2

Preparation of N-methacrylamidomethyl-L-proline - Cu(II) - L-serine Complex 1.71 g (7.3 mmole) L-methacrylamidomethyl-L-proline, 1.165 g (7.3 mmole) $CuSO_4$ and 0.767 g (7.3 mmole) L-serine are dissolved in 20 ml of distilled water. The pH is adjusted by means of 1M NaOH to 6.8. The solution is evaporated at reduced pressure and dried overnight in a desiccator. Subsequently, the dry residue is dissolved in 30 ml of methanol, and after filtering off inorganic salts, the methanol solution is evaporated at reduced pressure. 2.95 g (corresponding to a yield of 98% of the theoretical maximum) blue-coloured substance is obtained. $R_F$ 0.53 (methanol). Melting point: 172°–174° C. IR (cm$^{-1}$): 3500–3200, 2960–2850; 1680–1640 (strong); 1610–1550 (strong); 1550–1520; 1470–1430; 1420–1300.

Preparation of Polymer 6.8 mmole N-methacrylamidomethyl-L-proline - Cu(II) - L-serine complex is dissolved together with 5.24 g (34 mmole) N,N'-methylenebisacrylamide in distilled water to a total volume of 160 ml. 0.125 g (0.54 mmole) $(NH_4)_2SO_4$ is added together with 40 µl N,N,N',N'-tetramethyletylenediamine, and the solution is passed by nitrogen gas for a few minutes. After 4 h at room temperature, a gel-like polymer is obtained.

The polymer formed is isolated by filtration and is then allowed to sediment in 5 turns in distilled water, while removing the supernatant. The sediment is carefully washed with 1/1 95% ethanol/distilled water and distilled water to remove L-serine and is then dried in a desiccator overnight. Amino acid analysis after hydrolysis (6M HCl, 24 h, 110° C.) of a sample of the polymer proved that the polymer contains 64% of the theoretical amount of the proline derivative.

Chromatographic Evaluation

The polymer (1.4 g) is suspended in 50 ml 0.1M Cu(CH$_3$COO)$_2$, pH 5.3, is then washed in 5 turns with distilled water and is packed at a flow rate of 0.30 ml/min in distilled water in a low-pressure chromatography column (8×2.5 cm). 22 mg D,L-serine is applied in 0.5 ml distilled water, and the separation is carried out with the same eluant and at a flow rate of 0.30 ml/min. The eluate is collected in fractions of 1.45 ml. The contents of the two enantiomers in the fractions are determined by HPLC analysis after derivatising with (+)-1-(9-fluorenyl)ethylchloroformate (See S. Einarsson, B. Josefsson, P. Möller and D. Sanchez, Anal. Chem., Vol. 59, 1191–1195, 1987). The analysis showed that the fractions 7, 8, 9, 10 and 11 contained 100% D-serine, the fractions 12, 13, 14 and 15 96% D-serine and 4% L-serine; the fractions 18, 19 and 20 95% D-serine and 5% L-serine.

What is claimed is:

1. A method for preparing a molecular print polymer for adsorbing an enantiomer of a chiral nonderivatized amino acid, comprising:
   (A) preparing a diastereomeric complex between a monomer unit comprising an amino acid moiety, an enantiomer of a chiral nonderivatized amino acid, and a divalent metallic ion capable of forming a complex between said monomer unit and said enantiomer;
   (B) polymerizing the monomer moieties of said complex in the presence of a crosslinking agent; and
   (C) removing said amino acid from said polymerized complex, thereby obtaining said molecular print polymer.

2. The method as claimed in claim 1, wherein said chiral nonderivatized amino acid is naturally occurring.

3. The method as claimed in claim 1, wherein said chiral nonderivatized amino acid is synthetic.

4. The method as claimed in claim 1, wherein said monomer unit comprising an amino acid moiety is selected from the group consisting of N-methacrylamidomethyl-L-proline and N-methacrylamidomethyl-D-proline.

5. The method as claimed in claim 1, wherein said divalent metallic ion is selected from the group consisting of copper (II), manganese (II), iron (II), cobalt (II), zinc (II), cadmium (II), and nickel (II).

6. A molecular print polymer produced by the process of claim 1.

7. A molecular print polymer comprising:
   (A) a crosslinked polymerized monomer comprising an amino acid moiety;
   (B) a divalent metallic ion capable of forming a complex between said amino acid moiety of said monomer and an enantiomer of a chiral nonderivatized amino acid;
   wherein said polymer comprises affinity seats for said enantiomer, formed when said monomer is polymerized and crosslinked as a complex of said enantiomer and said divalent metallic ion.

8. The molecular print polymer as claimed in claim 7, wherein said monomer unit comprising an amino acid moiety is selected from the group consisting of N-methacrylamidomethyl-L-proline and N-methacrylamidomethyl-D-proline.

9. The molecular print polymer as claimed in claim 7, wherein said chiral nonderivatized amino acid is naturally occurring.

10. The molecular print polymer as claimed in claim 7, wherein said chiral nonderivatized amino acid is synthetic.

11. The molecular print polymer as claimed in claim 7, wherein said divalent metallic ion is selected from the group consisting of copper (II), manganese (II), iron (II), cobalt (II), zinc (II), cadmium (II), and nickel (II).

12. A process for separating an enantiomer of a chiral nonderivatized amino acid from a mixture thereof, comprising:
   (A) contacting a mixture comprising an enantiomer of a chiral nonderivatized amino acid with a molecular print polymer comprising:
      (1) a crosslinked polymerized monomer comprising an amino acid moiety;
      (2) a divalent metallic ion capable of forming a complex between said amino acid moiety of said monomer and an enantiomer of a chiral nonderivatized amino acid;
   wherein said polymer comprises affinity seats for said enantiomer, formed when said monomer is polymerized and crosslinked as a complex of said enantiomer and said divalent metallic ion;
   wherein said contacting occurs under conditions sufficient for said enantiomer to form a complex with said divalent metallic ion of said polymer; and
   (B) removing the enantiomer depleted mixture from contact with the polymer.

13. The process as claimed in claim 12, wherein said monomer unit comprising an amino acid moiety is selected from the group consisting of N-methacrylamidomethyl-L-proline and N-methacrylamidomethyl-D-proline.

14. The process as claimed in claim 12, wherein said chiral nonderivatized amino acid is naturally occurring.

15. The process as claimed in claim 12, wherein said chiral nonderivatized amino acid is synthetic.

16. The process as claimed in claim 12, wherein said divalent metallic ion is selected from the group consisting of copper (II), manganese (II), iron (II), cobalt (II), zinc (II), cadmium (II), and nickel (II).

17. The process as claimed in claim 12, wherein said enantiomer of said chiral amino acid is selected from the group consisting of D-proline and L-serine.

18. An amino acid-based monomer selected from the group consisting of N-methacrylamidomethyl-L-proline and N-methacrylamidomethyl-D-proline.

19. A method for preparing N-methacrylamidomethyl-L-proline and N-methacrylamidomethyl-D-proline, comprising condensing L-proline or D-proline, formalin, and methacrylamide under alkaline conditions.

* * * * *